United States Patent
DeMello et al.

(10) Patent No.: US 9,739,750 B2
(45) Date of Patent: Aug. 22, 2017

(54) OIL REMOVAL FROM A STREAM OF OIL-SEPARATED SAMPLE DROPLETS

(71) Applicant: ETH ZURICH, Zurich (CH)

(72) Inventors: Andrew DeMello, Zurich (CH); Fiona Pereira, London (GB); Niu Xize, London (GB)

(73) Assignee: ETH ZURICH, Zurich (CH)

( * ) Notice: Subject to any disclaimer, the term of this patent is extended or adjusted under 35 U.S.C. 154(b) by 227 days.

(21) Appl. No.: 14/416,838

(22) PCT Filed: Jul. 25, 2013

(86) PCT No.: PCT/EP2013/002202
§ 371 (c)(1),
(2) Date: Jan. 23, 2015

(87) PCT Pub. No.: WO2014/015984
PCT Pub. Date: Jan. 30, 2014

(65) Prior Publication Data
US 2015/0177187 A1 Jun. 25, 2015

(30) Foreign Application Priority Data

Jul. 26, 2012 (EP) .................................. 12005431

(51) Int. Cl.
*G01N 27/44* (2006.01)
*G01N 27/447* (2006.01)
(Continued)

(52) U.S. Cl.
CPC .. *G01N 27/44791* (2013.01); *B01L 3/502784* (2013.01); *E21B 43/34* (2013.01); *G01N 1/4005* (2013.01); *G01N 27/44743* (2013.01); *G01N 35/08* (2013.01); *B01L 2200/0673* (2013.01); *B01L 2300/0864* (2013.01); *B01L 2300/0877* (2013.01); *G01N 2001/4016* (2013.01)

(58) Field of Classification Search
None
See application file for complete search history.

(56) References Cited

U.S. PATENT DOCUMENTS

2010/0012586 A1* 1/2010 Angelescu ............ B01D 61/18
210/637

FOREIGN PATENT DOCUMENTS

GB          2417913 A          3/2006
GB          2474228 A          4/2011
(Continued)

OTHER PUBLICATIONS

International Search Report and Written Opinion for PCT/EP2013/002202 dated Nov. 20, 2013.

*Primary Examiner* — Chester Barry
(74) *Attorney, Agent, or Firm* — Pearne & Gordon LLP

(57) ABSTRACT

An oil removal device for removing oil from a stream (103) of oil-separated sample droplets (104) is disclosed. The oil removal device comprises a sample delivery channel (101) for conducting the stream of sample droplets to an outlet (102). A porous, hydrophobic and oleophilic absorber element (106) is arranged at the outlet of the sample delivery channel so as to absorb the oil phase (105) from the stream of oil-separated sample droplets. The oil removal device can be used in two-dimensional separation techniques such as LC-MS, LC-CE, CE-CE etc.

18 Claims, 7 Drawing Sheets

(51) Int. Cl.
*B01L 3/00* (2006.01)
*G01N 1/40* (2006.01)
*G01N 35/08* (2006.01)
*E21B 43/34* (2006.01)

(56) References Cited

FOREIGN PATENT DOCUMENTS

| | | | |
|---|---|---|---|
| WO | 2008097559 | A2 | 8/2008 |
| WO | 2009009185 | A2 | 1/2009 |

* cited by examiner

OIL REMOVAL FROM A STREAM OF OIL-SEPARATED SAMPLE DROPLETS

TECHNICAL FIELD

The present invention relates to a device and a method for removing oil from a stream of oil-separated sample droplets. In particular, the present invention relates to a device that is able to separate sub-nanoliter sample droplets from a continuous oil phase flowing through a microfluidic channel.

PRIOR ART

Mass spectrometry (MS), Capillary Electrophoresis (CE) and Liquid chromatography (LC) are among the most powerful tools in analytical and separation science, and are also widely used in physiology, pharmaceutics, diagnosis and therapeutics. Due to the complexity of biological samples, these approaches are often coupled for multiple dimensional separation and identification purposes (e.g. LC-MS, CE-MS, CE-CE). Whilst there has been much research and development surrounding the separation and identification mechanisms, sample injection and delivery between different modes has been much less studied, and in many cases represent the bottlenecks in high throughput or quantitative analysis.

For example, in CE, the two main injection methods (in both capillary and chip-based systems) are hydrodynamic and electrokinetic injection. Unfortunately, both of these approaches lack key features that ensure effective loading of "real" samples. For example, when using electrokinetic injection, bias occurs at the injection point since analyte molecules have different mobilities. Hydrodynamic injections on the other hand suffer from a lack of control with respect to the volume delivered during the injection, and the overall throughput of the device. It should also be noted that although the injection zones in CE tend to be less than 10 nL, the actual sample needed for performing a separation is significantly higher (>10 µL). Therefore the majority of the sample is not analyzed. Finally, conventional platforms are ill-suited to the analysis of more than one sample (simultaneously or sequentially) due to problems of surface contamination.

MS, and in particular MALDI-MS, is capable of identifying a wide range of biological samples. However, this ability is compromised when complex sample mixtures are investigated. For example, the mass spectrum of low abundance molecule if often swamped by signals from more abundant species. To reduce sample complexity, MS is often coupled to one or more separation techniques either in an on-line or off-line format (e.g. LC-MS, CE-MS). Therefore sample or fraction transfer between separation modes is necessary and conventionally achieved using thin capillaries and in continuous flow. However, band broadening and re-mixing of samples is difficult (and almost impossible) to avoid.

Re-mixing of samples during sample transfer (between separation modes) can be avoided by digitisation of the initial continuous flow into a segmented flow containing oil-separated sample droplets. Droplets act as ideal isolated reactors and can be used to encapsulate small molecules, biomolecules, cells and organisms. Furthermore droplets can be generated and detected in a high-throughput manner allowing rapid online screening and detection of the contained molecules. However, there have been no reports on how to subsequently and completely remove the continuous oil phase and deposit those droplets onto a MALDI plate.

Traditionally, centrifugation is used to separate the aqueous phase from the oil phase after droplet manipulations. After centrifugation, all of the microdroplets are merged into one unit with much bigger volume or merged into an additional amount of preloaded aqueous phase. Such a scheme will unavoidably lose the identity of single droplets, which is a key advantage when processing such droplets.

Another approach reported is to inject droplets into a continuous micro flow, which flows in another stream, while keeping the remaining oil flow in the original stream (e.g. L. M. Fidalgo, G. Whyte, D. Bratton, C. F. Kaminski, C. Abell and W. T. S. Huck, Angew. Chem. Int. Ed. 2008, 47, 2042-2045; M. Wang, G. T. Roman, M. L. Perry, and R. T. Kennedy, Analytical Chemistry 81, 9072-9078 (2009)). Such methods can fuse droplets into a continuous phase, but suffer from significant dilution of the sample and difficulties in controlling the oil outlet flow without disturbing or contaminating the aqueous channel.

It has also been suggested to directly inject droplets into an aqueous separation channel by reversibly penetrating and resealing the immiscible partition (J. S. Edgar, C. P. Pabbati, R. M. Lorenz, M. He, G. S. Fiorini, and D. T. Chiu, Anal. Chem. 78, 6948-6954 (2006)). However, such an approach is not well suited for injecting a continuous stream of oil-separated droplets into the aqueous channel.

GB 2474228 and X. Z. Niu, B. Zhang, R. T. Marszalek, O. Ces, J. B. Edel, D. R. Klug and A. J. deMello, Chemical Communications, 2009, 6159 suggested removing the oil phase into a side channel with the aid of pillar elements that effectively form a barrier for aqueous droplets while being oil permeable. The oil is recovered as a continuous stream, which is actively aspirated by applying suction to the side channel. A delicate pressure balance across the pillar elements is needed to prevent aqueous liquid entering the side channel, or prevent oil remaining in the aqueous droplet stream.

GB 2417913 discloses a microfluidic separator wherein two immiscible liquids such as oil and water are separated by a porous membrane. The liquid that permeates through the membrane (generally the oil phase) is recovered as a continuous stream in a separate channel. Again, delicate pressure balance across the membrane is required.

SUMMARY OF THE INVENTION

In a first aspect, it is an object of the present invention to provide an oil removal device for removing oil from a stream of oil-separated sample droplets, which is simple in construction, easy to operate, and which can achieve substantially complete oil removal.

This object is achieved by an oil removal device as laid down in claim 1.

In a second aspect, it is an object of the present invention to provide a corresponding method of oil removal.

This object is achieved by method as laid down in claim 12.

Further embodiments of the invention are laid down in the dependent claims.

According to the invention, an oil removal device is provided for removing oil from a stream of oil-separated sample droplets. The oil removal device comprises at least one sample delivery channel for conducting the stream of sample droplets, which are separated by an oil phase. The oil removal device further comprises a porous, hydrophobic and oleophilic absorber element, the absorber element being in contact with the sample delivery channel so as to absorb the oil phase from the stream of oil-separated sample droplets.

In this manner, very simple oil removal can be achieved without requiring delicate pressure balance across a separating structure like the membranes or pillar elements known from the prior art, which do not act as absorbers.

The sample droplets will in the following be referred to as "aqueous droplets" or as an "aqueous phase". Indeed, often the droplets will contain water as a solvent; however, it is also conceivable to use other solvents that are immiscible with oil, such as acetonitrile or DMSO or other organic solvents. Therefore, in the present context, an "aqueous liquid" or "aqueous phase" is to be understood broadly as encompassing not only water-based liquids, but also liquids that are readily miscible with water, as long as the liquid is immiscible with oil. Likewise, if a structure is labeled with reference to an aqueous phase, such as in the term "aqueous flow channel", such a structure is to be understood as being suited for carrying an aqueous phase in the above sense.

The sample delivery channel is preferably a microchannel having lateral dimensions between 1 μm and 1000 μm, for example between 50 μm and 500 μm. The channel walls are preferably made of a material that has a better wettability for the oil phase than for the aqueous phase. In particular, the oil phase should wet the channel wall surface, while the aqueous phase should not. Suitable materials include modified glass made hydrophobic by appropriate surface modification and polymers including polymeric organosilicon compounds, in particular, polydimethylsiloxane (PDMS). The sample delivery channel may, for example, be fabricated from PDMS using known lithography methods. In the alternative, the sample delivery channel may be formed by a piece of tubing, in particular, tubing made of a hydrophobic material such as polytetrafluoroethylene (PTFE), or by a capillary, e.g., a glass capillary having a chemically modified inside surface.

The absorber element is porous, i.e. it defines a three-dimensional network of pores, in particular, an irregular three-dimensional network of pores, as in solid foams. Methods for obtaining solid foams with a certain pore size distribution are well known in the art. In some embodiments, however, the pores of the absorber element may be obtained by microfabrication methods such as micromachining, laser ablation, thermal ablation, and chemical methods such as chemically guided etching.

The largest pores of the absorber element (at least in those surface portions of the absorber element which face the sample delivery channel, i.e., at the interface to the stream of oil-separated sample droplets) should be smaller than the size of the sample droplets, in particular, smaller than the lateral dimensions of the sample delivery channel, preferably by at least a factor of 10, so as to avoid entry of the sample droplets into the pores of the absorber element. Preferably, the maximum dimension of the pores at the surface of the absorber element that faces the sample delivery channel is between 100 nm and 1 μm, in particular, between 200 nm and 600 nm.

The absorber element is hydrophobic and oleophilic. A material is hydrophobic if its surface is not wetted by water. In particular, its surface should have a contact angle for water which exceeds 90° and preferably exceeds 110°. A material is oleophilic if its surface is readily wetted by oil. In particular, its surface should have a contact angle for standard oils below 90° and preferably below 60°.

Only those surface portions of the absorber element which face the sample delivery channel (in particular, its surface portions facing the sample delivery channel) are required to be both hydrophobic and oleophilic, whereas those portions of the absorber element which are removed from the sample delivery channel do not need to be hydrophobic, since they do not get in direct contact with the sample droplets. In particular, the absorber element can comprise two parts, a first part, which faces the sample delivery channel, being porous, hydrophobic and oleophilic, while a second part, which does not face the sample delivery channel, may be porous and oleophilic, but does not necessarily need to be hydrophobic.

The absorber element can be entirely made of a porous hydrophobic and oleophilic material, e.g. of porous bulk PTFE or of a material known as Smart Sponge™ available from AbTech Industries, Inc. In the alternative, the absorber element can be made of a porous scaffold coated by a hydrophobic and oleophilic material. Suitable materials for the scaffold include polyethylene terephthalate (PET), polyethylene (PE) and polyurethane (PU). Suitable coating materials include silanes and fluoropolymers such as TEFLON™ AF amorphous fluoropolymer available from DuPont (www.dupont.com) or CYTOP™ amorphous fluoropolymer available from AGC Chemicals Europe, Ltd., Amsterdam, Netherlands.

In order to ensure that the absorber element has sufficient capacity for absorbing the entire oil phase between two consecutive droplets, the absorber element preferably has dimensions in all spatial directions that exceed the maximum lateral dimension of the sample delivery channel at its outlet. In particular, the absorber element preferably has a thickness (measured along a direction that is orthogonal to the first flow direction) that exceeds the maximum lateral dimension of the sample delivery channel at the position of contact with the absorber element. The total pore volume or the oil-absorbing capacity of the absorber element should exceed the typical volume of oil between two consecutive sample droplets. In particular, the total pore volume or oil-absorbing capacity should exceed a volume corresponding to the third power of the square root of the cross-sectional area of the sample delivery channel and should preferably exceed at least 10 times, and more preferably at least 100 times the latter volume.

The absorber element is preferably entirely passive, without any active withdrawal of the absorbed oil. In particular, the absorber element does not need to be connected to any kind of suction source. In other embodiments, the oil removal device can comprise an oil withdrawal channel for withdrawing oil from the absorber element and optionally a source of suction such as a vacuum pump for actively withdrawing the oil. In this case there is no need to replace the absorber element once it has reached its maximum oil-absorbing capacity.

In order to not unnecessarily impede the flow of the sample droplets, the absorber element is preferably arranged in a laterally offset configuration relative to the center of the sample delivery channel. More specifically, it is preferably arranged in a substantially tangential configuration relative to the first flow direction at the outlet of the sample delivery channel. In particular, the absorber element can have a surface extending essentially in line with at least one of the walls of the sample delivery channel at its outlet. Interaction of the stream of oil-separated droplets with the absorber element can be maximized by having the absorber element at least partially surround the outlet of the sample delivery channel.

The oil removal device may be used, e.g., for directly depositing the sample droplets onto a surface, e.g., onto a MALDI sample plate, or for directly injecting the sample droplets into a gas phase, as in electrospray MS. In such cases, the absorber element can itself delimit the outlet of the oil removal device, either partially or completely.

For other types of applications, such as LC or CE, it can be desired to merge the droplets, or to inject the droplets one-by-one into a stream of carrier liquid, preserving droplet identity. For such purposes, the oil removal device can further comprise an aqueous flow channel for conducting a stream of aqueous liquid, the aqueous flow channel having a droplet inlet arranged to receive sample droplets from the outlet of the sample delivery channel.

For some applications, it is sufficient to simply merge consecutive sample droplets after oil removal, such that the sample droplets themselves form a continuous aqueous stream in the aqueous flow channel. In this case, the droplet inlet may form the upstream end of the aqueous flow channel.

For other applications, it may be desired to inject the droplets into an aqueous stream of a carrier liquid while preserving droplet identity. For such applications, the aqueous flow channel can have a carrier liquid inlet arranged upstream of the droplet inlet, in particular, at an upstream end of the aqueous flow channel, for receiving a continuous stream of aqueous carrier liquid. The carrier liquid is conducted through the aqueous flow channel along a second flow direction, and the sample droplets that are received at the droplet inlet are injected into the stream of aqueous carrier liquid.

Preferably, at the droplet inlet, the second flow direction (i.e. the direction of flow of the carrier liquid) extends non-parallel and preferably substantially transverse to the first flow direction (i.e. the direction of flow of the stream of oil-separated sample droplets), in particular, at an angle between 45° and 135°, preferably between 60° and 120°, more preferably approximately 90° relative to the first flow direction. In other words, the sample delivery channel and the aqueous flow channel can form essentially a T-junction.

A particularly simple, yet effective construction can be achieved if the aqueous flow channel and the absorber element, at the droplet inlet, are each arranged in a laterally offset configuration relative to the sample delivery channel, the aqueous flow channel and the absorber element being arranged on mutually opposite sides of the sample delivery channel. In this manner, the directions of flow of the sample droplets and of the oil phase are well separated at the droplet inlet. Furthermore, this provides for a constructional simplicity of the oil removal device, wherein the aqueous flow channel is formed by a groove in a substrate. The sample delivery channel may then be formed by a piece of tubing or a capillary lying flat on the substrate and extending transversely to the groove, the end of the tubing or capillary forming the outlet of the sample delivery channel and being arranged just on top of the groove. The absorber element can then be disposed on top of the tubing, facing the substrate.

For the dimensions of the aqueous flow channel, similar considerations apply as for the sample delivery channel. In particular, the aqueous flow channel is preferably a microchannel having lateral dimensions between 1 μm and 1000 μm, for example between 50 μm and 500 μm. The droplet inlet preferably has a width and length roughly commensurate with the lateral dimensions of the sample delivery channel, in particular, between 1 μm and 1000 μm, for example between 50 μm and 500 μm.

The walls of the aqueous flow channel should be hydrophilic and can be made of glass and/or hydrophilic polymers. The aqueous flow channel may, for example, be fabricated from PDMS using known lithography methods and be surface-modified to render the channel hydrophilic. In the alternative, the aqueous flow channel may be delimited by a piece of tubing, or fused silica capillary.

The aqueous flow channel can be used directly as a container for analytical schemes. In particular, the aqueous flow channel can directly form a detection channel for electrophoretic analysis or may be connected to a CE capillary arranged downstream of the droplet inlet. In that case, the lateral dimensions (in particular, the cross-sectional area) of the aqueous flow channel should preferably at least roughly correspond to the lateral dimensions of the CE capillary.

In particular, the invention provides an electrophoretic separation device comprising an oil removal device having an aqueous flow channel as described above, and at least two electrodes for inducing electrophoresis in the aqueous flow channel along the second flow direction.

A corresponding method of removing oil from a stream of oil-separated aqueous sample droplets comprises:
  conducting the stream of sample droplets separated by an oil phase through a sample delivery channel; and
  absorbing the oil phase from the stream of oil-separated sample droplets by a porous, hydrophobic and oleophilic absorber element in contact with the sample delivery channel.

The sample droplets can have a volume ranging from the attoliter range to the microliter range. Preferably the volume is in the femtoliter to the lower nanoliter range (approximately $10^{-12}$-$10^{-8}$ liters). The length of the droplets in the sample delivery channel is preferably between 5 μm and 2 mm.

Representative oils useful as the oil phase include carbon-based oils, silicone-based oils, and fluorinated oils. Representative examples of oils useful in the invention include embryo-tested mineral oil, light mineral oil, heavy mineral oil, PCR mineral oil, AS4 silicone oil, AS 100 silicone oil, AR2O silicone oil, AR 200 silicone oil, AR 1000 silicone oil, AP 100 silicone oil, AP 1000 silicone oil, AP 150 silicone oil, AP 200 silicone oil, CR 200 Silicone oil, DC 200 silicone oil, DC702 silicone oil, DC 710 silicone oil, octanol, decanol, acetophenone, perfluoro-oils perfluorononane, perfluorodecane, perfluorodimethylcylcohexane, perfluoro-1-butanesulfonyl fluoride, perfluoro-1-octanesulfonyl fluoride, perfluoro-1-octanesulfonyl fluoride, nonafluoro-1-butanesulfonyl chloride, nonafluoro-tert-butyl alcohol, pertluorodecanol, perfluorohexane, perfluorooctanol, perfluorodecene, perfluorohexene, perfluorooctene, fuel oil, halocarbon oil 28, halocarbon oil 700, hydrocarbon oil, glycerol, 3M Fluoriner™ fluids (FC-40, FC-43, FC-70, FC-72, FC-77, FC-84. FC-87, FC-3283), soybean oil, castor oil, coconut oil, cedar oil, clove bud oil, fir oil, linseed oil, safflower oil, sunflower oil, almond seed oil, anise oil, clove oil, cottonseed oil, corn oil, croton oil, olive oil, palm oil, peanut oil, bay oil, borage oil, bergamot oil, cod liver oil, macadamia nut oil, camada oil, chamomile oil, citronella oil, eucalyptus oil, fennel oil, lavender oil, lemon oil, nutmeg oil orange oil, petitgrain oil, rose oil, tarragon oil, tung oil, basil oil, birch oil, black pepper oil, birch tar oil, carrot seed oil, cardamom oil, cassia oil, sage oil, cognac oil, copaiba balsam oil, cypress oil, eucalyptus oil, dillweed oil, grape fruit oil, ginger oil, juniper oil, lavender oil, tovage oil, majoram oil, mandarin oil, myrrh oil, neroli oil, olibanum oil, onion oil, paraffin oil, origanum oil, parsley oil, peppermint oil, pimenta leaf oil, sage oil, rosemary oil, rose oil, sandalwood oil, sassafras oil, spearmint oil, thyme oil, transformer oil, verbena oil, and rapeseed oil.

The oil preferably has a viscosity of between 5-500 cP at room temperature, for example between 5-300 cP at room temperature.

As explained in more detail above, the method may further comprise feeding sample droplets from an outlet of the sample delivery channel to a droplet inlet of an aqueous flow channel.

As also explained in more detail above, the method may further comprise:

conducting an aqueous carrier liquid through the aqueous flow channel; and injecting the sample droplets received at the droplet inlet into the stream of aqueous carrier liquid.

The aqueous carrier liquid may be an electrolyte solution, for example, be buffer or electrolyte in a CE channel.

Preferably each sample droplet has such a length in the sample delivery channel that, when a leading end of the sample droplet is positioned in the aqueous flow channel, a trailing end of the sample droplet still completely blocks the outlet of the sample delivery channel.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Example 1: Deposition Device for MALDI

Figure 1:
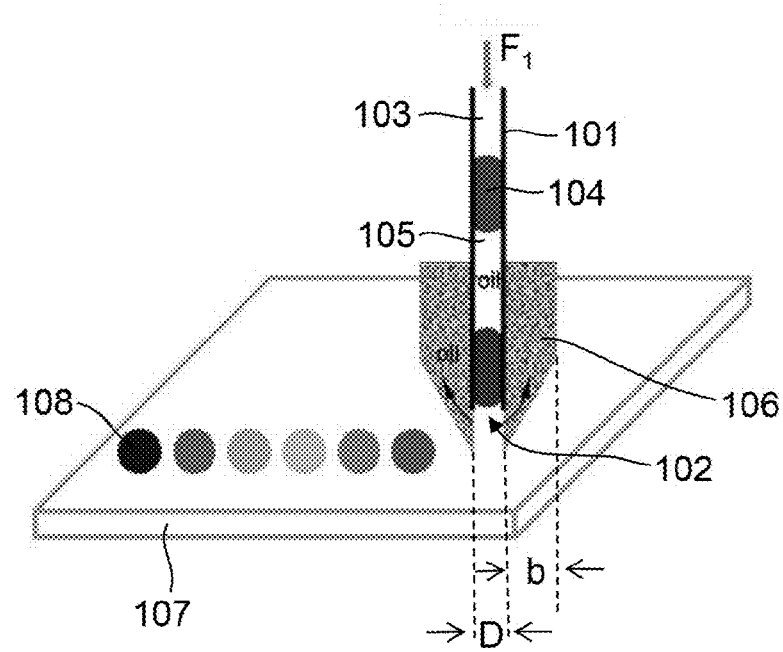
FIG. 1 shows, in a schematic view, a first embodiment of a device according to the present invention, which is suitable for depositing droplets onto a MALDI sample plate.

FIG. 1 illustrates a first embodiment of an oil removal device according to present invention (in the following also called a "droplet interface") and of a corresponding method of oil removal. A sample delivery channel 101 is formed by a piece of tubing, e.g. by 200 μm I.D. PTFE tubing. The sample delivery channel 101 conducts a stream 103 of droplets 104 separated by an oil phase 105 to an outlet 102 along a flow direction $F_1$. The outlet 102 is laterally surrounded by a porous, hydrophobic and oleophilic absorber element 106, e.g. in the form of porous PTFE. The absorber element 106 defines a three-dimensional, irregular array of pores. The absorber element 106 is arranged in a substantial tangential configuration relative to the flow direction $F_1$. In particular, the absorber element has a central bore, in which the tubing forming the sample delivery channel 101 is received, and the bore wall forms an inner surface of the bore, which extends essentially in line with the wall of the sample delivery channel at its outlet. In this manner the bore forms a continuation of the sample delivery channel. With the downstream end of the bore, the absorber element 106 forms the outlet of the oil removal device.

The absorber element 106 absorbs the oil phase 105 between the sample droplets 104 in the stream 103 of oil-separated sample droplets, while allowing the sample droplets 104 to pass the bore towards the outlet of the oil removal device essentially unimpeded.

The aqueous sample droplets consist of a solution of MALDI matrix mixed with an actual sample, e.g., with the effluent from a nano-liquid chromatography (nano-LC) column. Fractionation into droplets retains the resolution obtained during the LC separation. The sample droplets are deposited ("spotted") onto a solid surface in the form of a MALDI sample plate 107 with the aid of a standard x-y-z stage, as it is well known in the art. The dried droplets form individual, spatially separated sample spots 108 on the sample plate 107. In other words, the oil removal device acts at the same time as a deposition probe or spotting device for the droplets. In this manner, the oil removal device is part of an offline connection between a nano-LC instrument and a MALDI mass spectrometer.

In an alternative embodiment (not shown) the tubing that forms the sample delivery channel protrudes from the absorber element by 1 to 2 mm. In order to improve droplet formation, the end of the tubing may be cut at an angle, e.g., at a 30° angle. Deposition of the droplets onto the MALDI plate can be carried out by contacting the resulting tip to the surface of the plate.

Figure 2:
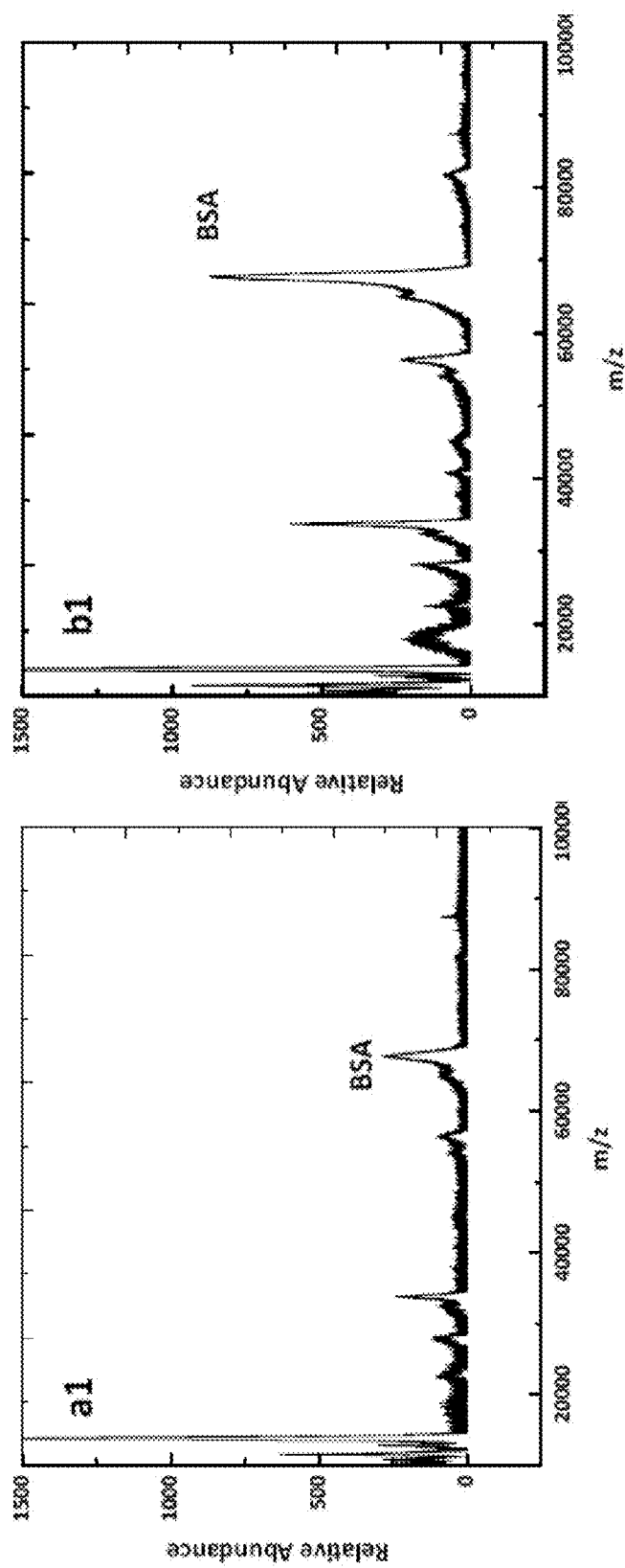
FIG. 2 shows MALDI-MS spectra of bovine serum albumin (BSA) obtained when spotted using the traditional dried drop technique (part a1) and obtained when using the device of FIG. 1 (part b1)

FIG. 2 shows MALDI-MS spectra of a BSA sample obtained when using the traditional dried drop technique (part a1) and of a BSA sample obtained when using the above-described alternative embodiment of a droplet interface device according to the present invention (part b1). The spectrum (b1) obtained with the device according to the present invention exhibits peaks in the expected mass-tocharge range and compares well with the spectrum (a1) of the control sample spotted using the traditional technique.

To obtain these spectra, a stock solution of BSA was prepared at a concentration of 7 mg/ml in 0.1% trifluoroacetic acid (TFA). The stock solution was diluted 1:1 in Sinapinic acid matrix prepared at a concentration of 12.5 mg/ml in 45% acetonitrile, 45% ethanol and ten percent 0.1% TFA. A stream of oil-separated droplets was generated using a traditional T-junction device. The aqueous phase was the above-described mixture of protein solution and MALDI matrix, while the oil phase was FC-40 oil. When samples were spotted using the droplet interface device according to the present invention, approximately 20 droplets of approximately 12 nL volume were collated per MALDI sample well. Mass analysis was carried out on a Micromass™ MALDI micro MX™ mass spectrometer (Waters, Manchester, UK). Positively charged ions were analysed in the linear mode. One hundred single-shot spectra were gathered manually in groups of 10 from random spots within each sample well on the MALDI plate. The spectra were summed and processed using the smoothing and base line correction functions provided in the Mass Lynx software.

Cross-contamination between droplets at the tip of the deposition probe and on the surface of the absorber element was investigated by observing fluorescence before, during and after spotting of droplets containing fluorescein isothiocyanate (FITC). No relevant cross-contamination was found.

Example 2: Merging of Droplets after Oil Removal

FIG. 2 illustrates a second embodiment of an oil removal device according to the present invention and of a corresponding method of oil removal. Parts having the same or similar functionality carry the same reference numbers as in FIG. 1. A stream 103 of oil-separated droplets 104 is transported to the outlet 102 of a sample delivery channel 101 formed by a first piece of PTFE tubing having an inner diameter D. The tubing protrudes into the upstream end of a central bore in a cylindrical, porous, hydrophobic and oleophilic absorber element 106. As in the first embodiment, the outlet 102 is surrounded by the absorber element 106, and the absorber element 106 is arranged in a substantial tangential configuration relative to the flow direction $F_1$, the bore in the absorber element forming a continuation of the sample delivery channel. From the downstream end of the bore, a second piece of PTFE tubing forming an aqueous flow channel 111 protrudes into the bore, the upstream end of the tubing forming a droplet inlet 112. The droplet inlet 112 has an axial distance d from the outlet 102 along the flow direction $F_1$, which should preferably be smaller than the length of the individual droplets. The absorber element 106 has an axial length L. The radial distance from the bore wall to the circumferential surface of the absorber element 106 is designated as the absorber thickness b. Optionally, the absorber element may be coated at its outside with a gastight coating, and a suction pump 120 may be connected to a suction opening in said coating for applying optional suction action to the absorber element.

In operation, the stream 103 of oil-separated aqueous droplets 104 reaches the outlet 102, where the oil phase 105 is absorbed by the absorber element 106 (see arrows in FIG. 2) whereas the aqueous droplets pass the bore in the absorber element 106 essentially unimpeded. The droplets are collected in the aqueous flow channel 111, where they merge to form a continuous stream of aqueous sample liquid flowing along a flow direction $F_2$, which in the present example is identical to the flow direction $F_1$.

Typical dimensions are as follows:

| | |
|---|---|
| diameter D | 50 μm-500 μm |
| distance d | 50 μm-500 μm |
| length L | 2 mm-50 mm |
| thickness b | 2 mm-50 mm |

However, the invention is not restricted to this range of values.

Example 3: Capillary Electrophoresis

Electrophoresis is one of the most powerful and widely used tools in separation science and has progressed significantly since its original development in 1937. Currently many different methods exist to perform electrophoretic separations (e.g. CZE, CGE, MEMKC, ETC, etc.). More recently, capillary and chip-based, microfabricated electrophoresis methods (CE/MCE) have been developed to provide automated analysis in a broad range of applications, within the fields of genomics, proteomics, metabolomics, enzyme analysis and cellonics. The advantages of CE/MCE are manifested in their ability to deal with small volumes, provide for high separation efficiency, be automated and coupled with the other methodologies, such as liquid chromatography (LC) and mass spectroscopy (MS).

FIGS. 3-6 illustrate embodiments of an oil removal device according to the present invention that are particularly adapted for interfacing a stream of oil-separated droplets to a CE or MCE device. Again, parts having the same or similar functionality carry the same reference numbers as in FIGS. 1 and 2.

Figure 3:
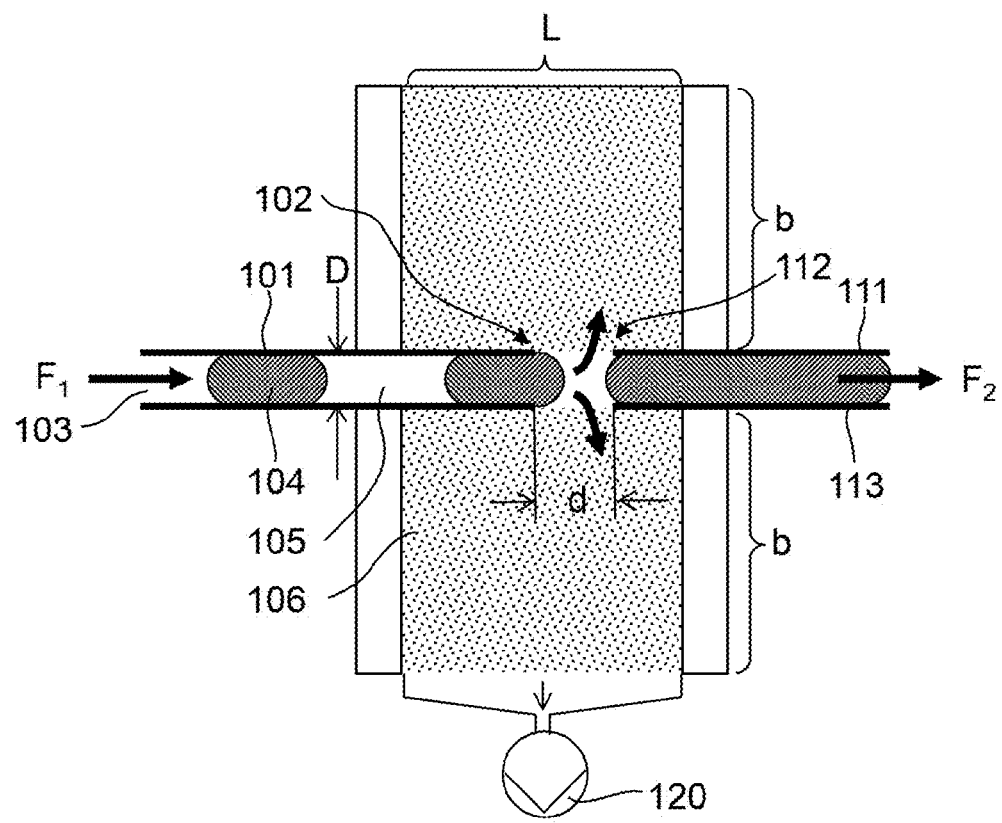
FIG. 3 shows, in a schematic view, a second embodiment of a device according to the present invention, wherein the sample droplets are merged and collected in an aqueous flow channel.
Figure 4:
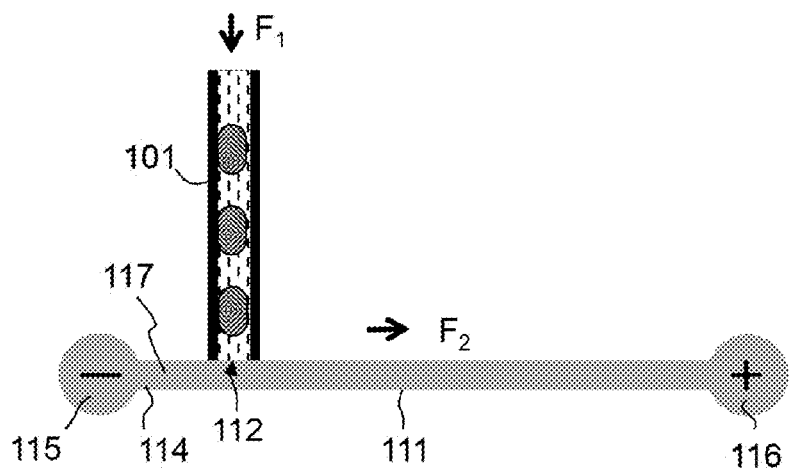
FIG. 4 shows, in a schematic view, an electrophoretic device including a third embodiment of an oil removal device according to the present invention, wherein the sample droplets are injected into a stream of carrier liquid and subjected to capillary electrophoresis.

FIG. 3 shows, in a highly schematic manner, a plan view of an MCE separation platform. FIG. 4 shows, in a highly schematic manner, a cross sectional view through the platform from the left, in a plane orthogonal to the viewing plane of FIG. 3 that contains the center axis of the sample delivery channel 101.

The separation platform comprises an aqueous flow channel (separation channel) 111 (length 6 cm) and a droplet injection device acting at the same time as an oil removal device according to the present invention. The aqueous flow channel 111 and the tubing that forms the sample delivery channel 101 were joined by a junction which is located 6 mm downstream from a buffer reservoir 115 feeding an aqueous carrier liquid 117 to a carrier liquid inlet 114. The aqueous flow channel 111 was made from PDMS using conventional soft lithographic techniques by bonding a PDMS substrate 118 having a groove to a bottom PDMS layer (not shown) after plasma treating the surfaces. The aqueous flow channel 111 was filled with either a buffer or sieving matrix for free-zone or gel electrophoresis, respectively. In order to perform the separation an electric field was applied between the buffer reservoir 115 and a sample waste reservoir 116 using platinum electrodes disposed in these reservoirs. Thin-walled PTFE tubing with an inner diameter of either 50 μm or 200 μm was used for the sample delivery channel 101.

The injection of sample droplets from the sample delivery channel 101 into the aqueous flow channel 111 occurred via an aperture forming a droplet inlet 112 at the interface between the channel junctions. This aperture was obtained by removing an area of PDMS from the bottom layer prior to plasma bonding, resulting in an elongated window with a direction of elongation perpendicular to the flow direction $F_2$ in the aqueous flow channel 111. The PTFE tubing of the sample delivery channel 101 was placed in the window in such a manner that the downstream end of the tubing, which formed the outlet of the sample delivery channel 101, was placed just below the aqueous flow channel 111 (FIG. 4). The end of the tubing was cut at a 30° angle, with the cut surface directed towards the aqueous flow channel 111. This ensured efficient transport of the sample droplets 104 into the aqueous flow channel 111.

In order to ensure that the oil phase separating the sample droplets was removed, an absorber element 106 comprising a hydrophobic and oleophilic foam was positioned near the channel junction just below the downstream end of the sample delivery channel 101, in a laterally offset configuration relative to the sample delivery channel 101 on the opposite side of the aqueous flow channel 111. The foam consisted of a porous, hydrophobic and oleophilic PTFE material with a mesh size of less than 5 µm and a thickness b of 200 µm, obtained from Whatman™ (Maidstone, Kent, UK). The absorber element 106 further comprised a polyester cleanroom paper 109 (approximately 150-200 g/m²), which supported the foam. This allowed for the hydrophobic oil to be absorbed and be transported through the foam whilst allowing the aqueous droplets to be delivered into the aqueous separation channel 111.

It was found that when using a 10 mm×10 mm×1 mm piece of foam, more than 200 µL of FC-40 oil could be absorbed in the foam. This volume corresponds to a total volume of the sample droplets of 20 µL, corresponding to approximately 10,000 individual droplets (assuming an oil/sample occupancy ratio of 10:1 in the PTFE tubing and average droplet size of 2 nL). In the rare event that sampling above this number is required, the foam could be regenerated or simply replaced. However, such a large droplet number is generally far more than needed when performing almost all conventional analyses and makes large scale integration and parallelization a realistic prospect.

No surfactant was added to the oil phase (FC-40 in all of the experiments carried out). When the (roughly spherical) droplets made contact with the aqueous buffer in the aqueous flow channel 111, droplet merging occurred on a sub-millisecond time scale.

Figure 5:
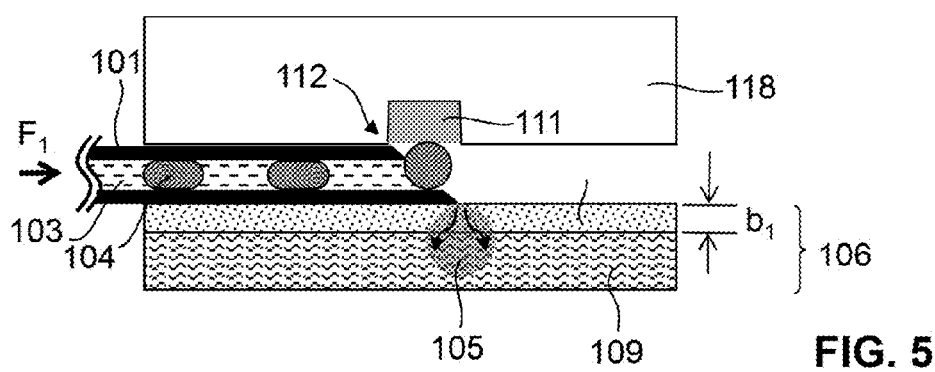
FIG. 5 shows a details view of the junction region in the device of FIG. 4.
Figure 6:
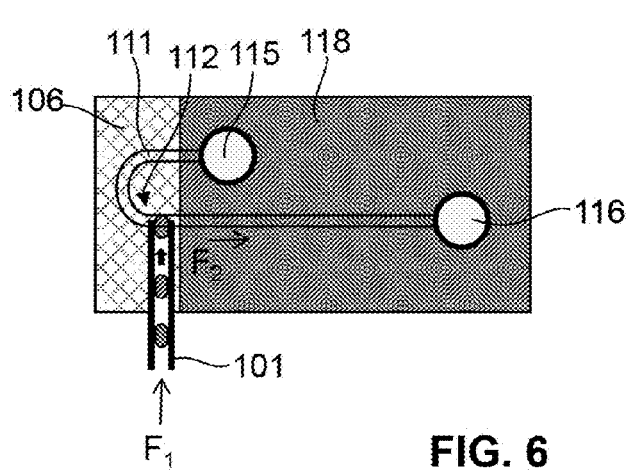
FIGS. 6 and 7 show two variants of the device of FIG. 4.

Two separation platforms were designed according to the principles of FIGS. 3 and 4 to accommodate both CZE (capillary zone electrophoresis) and CGE (capillary gel electrophoresis) separations. In the embodiment of FIG. 5, the aqueous flow channel 111 acting as the CE separation channel was composed of PDMS material alone. Such a design proved suitable for CZE separations since the buffer could be easily filled from the reservoirs after plasma bonding. On the other hand, for performing CGE, a fused silica capillary 119 pre-filled with gel, acting as the separation channel, was inserted into an appropriately widened channel in the substrate 118 (FIG. 6). The widened channel had a cross section of 300×150 µm² for easy insertion of the capillary 119. The main difference between the CZE and the CGE device formats was in the separation channel; the injection parts of each device were identical. During the sample injection process, an electrical field of 200 V/cm (used for separation) was maintained throughout. Consequently separation of the molecules within each injected sample droplet occurred immediately after injection, without any alteration of the electric field.

Figure 7:
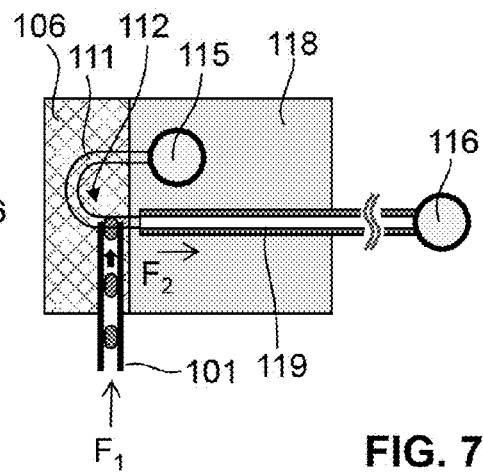

In initial studies, droplet injection was calibrated using the device shown in FIG. 5. The droplets had a volume of 80 pL and 1.2 nL, respectively, and contained 500 µM Fluorescein iso-thiocynate (FITC) in ×0.1 TBE, surrounded by an FC-40 oil phase. Droplets were pre-generated with a homemade robotic head and stored in PTFE tubing with an inner diameter of either 50 µm or 200 µm. The relative standard deviation in droplet volume for both sizes was measured to be approximately 4% (determined over 600 droplets). For experiments, individual droplets were sequentially injected into the aqueous flow channel (separation channel) every 10 seconds. FIG. 7 shows the fluorescence signal of a sequence of 80-picoliter droplets with uniform size and speed, measured at the end of the sample delivery channel tubing just prior to the junction with a separation channel with a cross section of 50×50 µm². Importantly, after this injection, and a further 90 subsequent injections, which are not shown, no fluorescence dye contamination was found either at the injection point or in the PTFE tubing of the sample delivery channel.

It was found that there was an optimal range of droplet sizes for reliable droplet injection. For example, with 200 µm i.d. tubing, and a flow speed of 50 µm/s, a droplet with a length less than 500 µm could jump into the separation channel as a whole. Above that length, the droplet tended to break during jumping due to Plateau-Rayleigh instability, leaving a sister droplet in the sample delivery channel. The "critical" length of sample droplets will of course depend on the lateral dimensions of the sample delivery channel.

An important advantage of the current design is its ability to enable multiple injections of droplets into the separation channel, without accumulation of buffer at the junction. This is significant since buffer accumulation will dilute the sample and stagger its entrance into the separation channel, thereby reducing the overall resolution. This feature relies on the different surface tensions defined by channel geometries. At the junction area, the buffer is confined within three solid walls; therefore a curvature exists at the open side. This curvature can be either concave or convex, depending on whether the liquid is below or above the open surface. The local pressure at the liquid surface due to surface tension is inversely proportional to the radius of the curvature. Such a pressure has a tendency of minimizing the total surface area. In the other words, if the liquid is above the open surface (i.e. during sample droplet injection), the pressure tends to push the liquid into the channel. When the liquid is below the surface (which can happen due to evaporation), the pressure tends to pull supplementary liquid out. As shown in FIGS. 3, 5 and 6, the aqueous flow channel 111 is closely connected to the buffer reservoirs 115, 116. Because each reservoir has an opening much larger than the channel width (2 mm compared with 25 or 50 µm), the surface tension in the reservoir is almost negligible compared to the surface tension at the junction. Therefore redundant and supplementary liquid can flow to or be provided by the buffer reservoir. This ensures a continuous injection of droplets into the separation channel.

Capillary zone electrophoresis separations were performed using a PDMS microchannel as shown in FIG. 5. The separation channel was initially loaded with 1 M NaOH, which was replaced with a ×0.1 TBE (pH 8.3) run buffer prior to separation. A conductivity check was performed to ensure electrical connection between the inlet and outlet reservoir, and an electric field was applied for 4 minutes to stabilize the electro-osmotic flow (EOF) in the channel. Droplet flow rates were set to 0.1 µL/min, which resulted in droplets being injected into the separation channel every 35 seconds. Injected droplets formed discrete sample plugs and migrated with the EOF downstream towards the detector.

Figure 8:
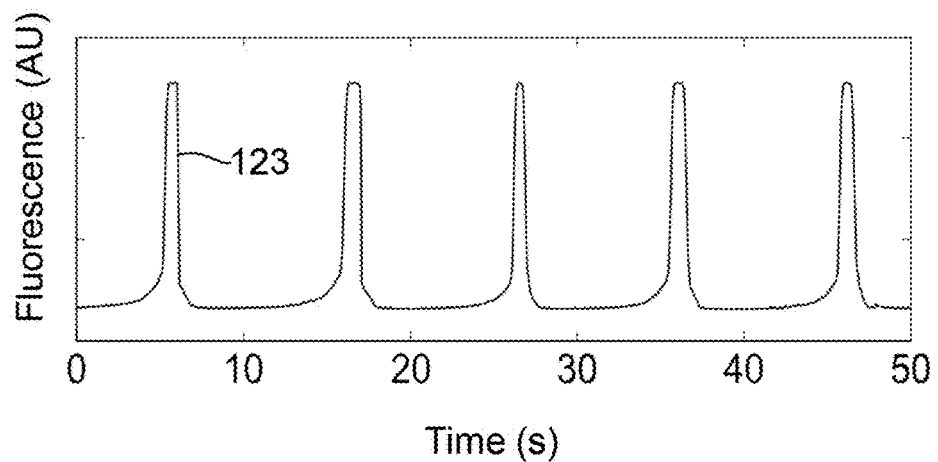
FIG. 8 shows fluorescence signals of consecutive droplets containing a fluorescent dye immediately before injecting the droplets into a stream of carrier liquid.

Fluorescein iso-thiocynate (FITC) and Eosin Y solutions at final concentrations of 100 μM and 500 μM, respectively, were prepared as a mixture in ×0.1 TBE (pH 8.3). At this pH both dyes are negatively charged and migrate behind the EOF. Separation was performed by applying a field strength of 266.6 V/cm between the buffer and waste reservoirs. Example electropherographs are shown in FIG. 8. The percentage RSD values for mobility of Eosin Y and FITC over 30 injections were 7.9% and 8.9% respectively, which demonstrate excellent reproducibility.

CZE is the most universal electrophoretic technique, being used to separate a diversity of analytes including ions, small molecules, peptides, proteins and carbohydrates. Alternate separation modes such as MEKC, CEC and CIEF can provide enhanced separation in certain circumstances with an identical sample loading process. Accordingly the described droplet interface can be applied with minimal modification to those separation modes.

Capillary gel electrophoresis (CGE), or more generally capillary sieving electrophoresis (CSE), can separate DNA and proteins through media containing selective physical barriers like polydimethyl acrylamide (pDMA) gel, polyethylene oxide (PEO) or dextran. Such sieving media provide frictional forces to differentiate molecules by size, which in combination with electrophoretic forces allows high resolution separations of large biomolecules. However, most sieving matrices are typically very viscous, and loading the gel or sieving matrix into the channel requires application of high pressures. This is not ideal for the droplet interfaced channels which contains an open part. Moreover, the position of the gel inside the channel cannot be easily monitored and controlled. To solve these challenges, a hybrid interface was adopted by connecting the PDMS chip to a fused silica capillary, as shown in FIG. 6. The droplet injection part was identical to that used in the CZE mode (FIGS. 4 and 5), but the separation channel was shortened and replaced with a 300 μm wide channel that allow insertion of the capillary. The capillary employed had a 100 μm inner diameter and 375 μm outer diameter; it was filled with 2.5% PEO gel in 8.9 mM Tris, 8.9 mM borate and 0.2 M EDTA buffer after surface conditioning. The PDMS bottom layer under the outlet allowed the capillary to be inserted smoothly and without chip delamination. With the described buffer-gel format, there was no bulk flow in the capillary, because EOF is retarded by the use of a PVP pre-coat and a high viscosity gel. During operation, any EOF in the open part of the channel might damage the connection, either by disconnecting the channel if the EOF is flowing towards the TBE buffer reservoir, or by accumulating buffer at the opening of the capillary. Therefore, after chip bonding, the separation channel was filled with deionised water, which was then replaced with TBE buffer prior to operation. Such a process was found to suppress the EOF effectively.

Figure 9:
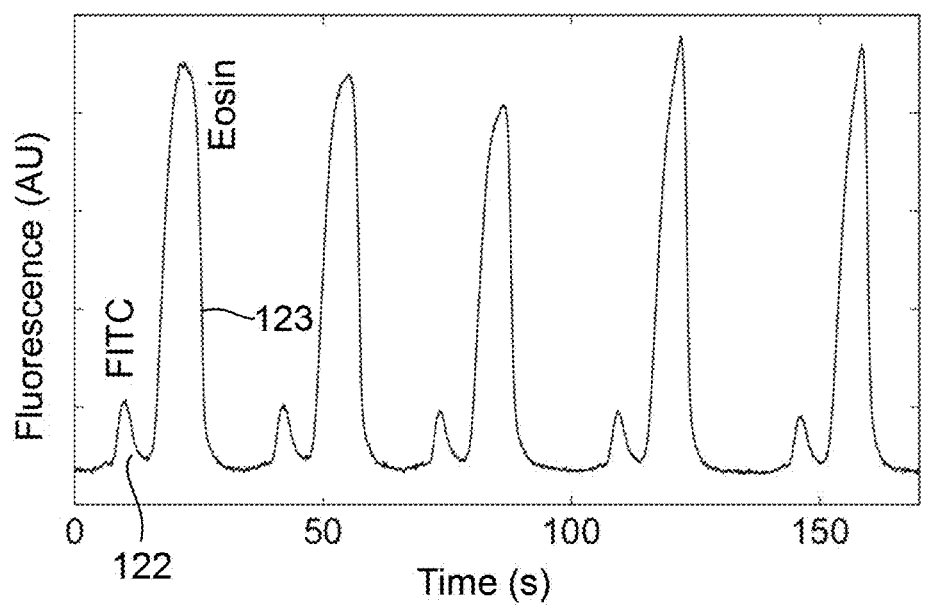
FIG. 9 shows an electropherogram for droplets containing an FTIC/Eosin mixture, the droplets having been injected into a stream of carrier liquid and subjected to capillary electrophoresis.

A 50 bp dsDNA molecular weight standard was used to assess the performance of the droplet interface, as shown in FIG. 9. Fourteen out of sixteen fragments of the fragment ladder could be unambiguously identified. Detection was performed 1.1 cm downstream of the point of injection. The sixteen fragments and the 1800 bp "backbone" fragment were separated within 55 seconds for each injection.

Figure 10:
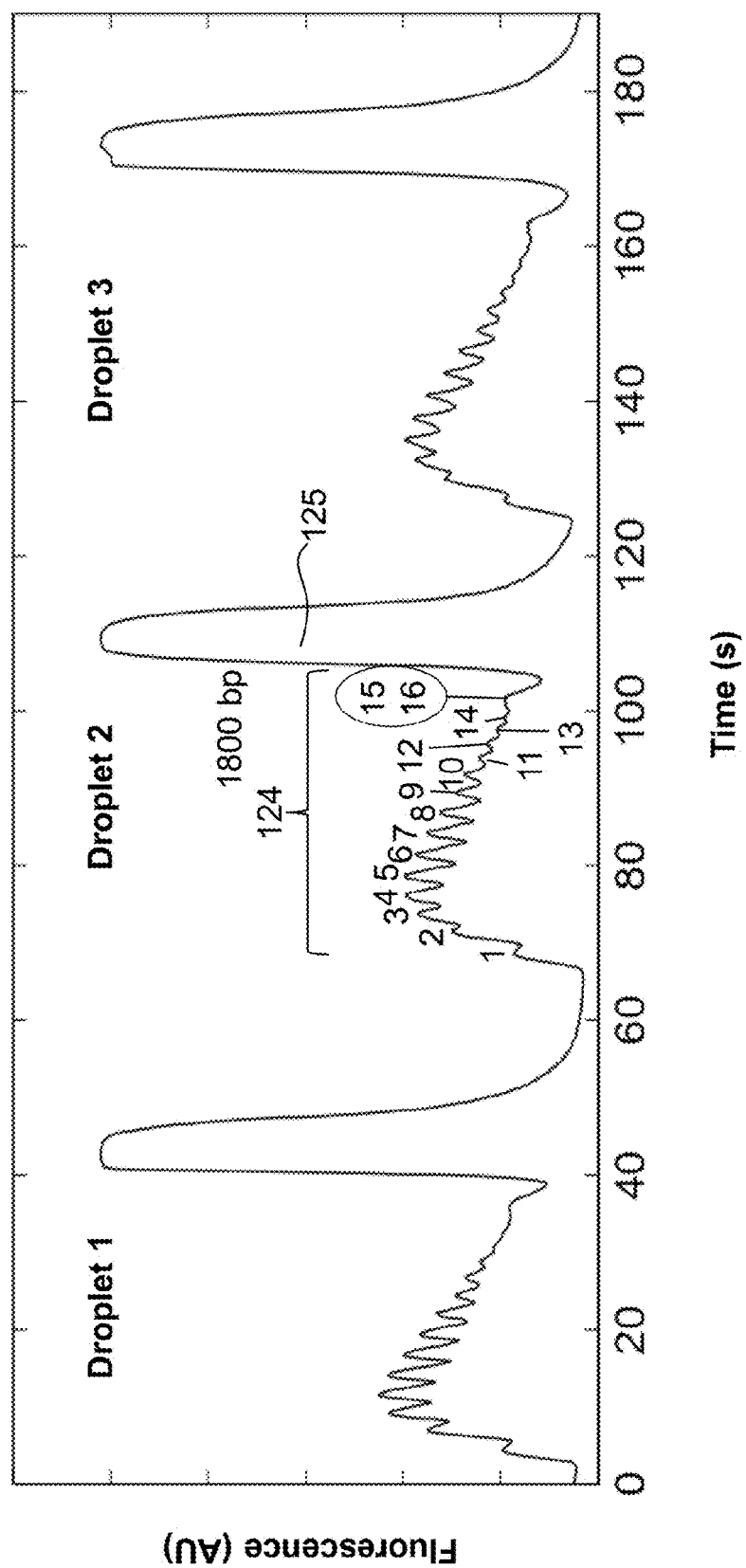
FIG. 10 shows an electropherogram for droplets containing a 50 bp dsDNA molecular weight standard, the droplets having been injected into a stream of carrier liquid and subjected to capillary electrophoresis.

A plot of mobility versus fragment size for each injection is shown in FIG. 10. Each zone (I, II, III) marked in FIG. 10 corresponds to a specific sieving mechanism. The lower molecular weight fragments undergo Ogston sieving (zone I), while the section of the curve showing an exponential decrease in mobility values corresponds to a reputation mechanism of migration (zone II). Here the fragment mobility is inversely proportional to its molecular weight or length. Above a specific size the dsDNA fragments align with the applied field reducing the difference in mobility values obtained between them. This migration mechanism is described by biased reputation theory (zone III). All three droplets followed a similar trend described by the three possible sieving mechanisms.

The multiple injection results presented in FIG. 9 were only part of a larger group of sample droplets. Over the repeats, the mobility values of the fragments varied between 2% to 10%. Larger variation was observed for the smaller fragments, due to stretching of matrix pores by the larger fragments of a prior injection. The sieving matrix degraded with repetitive use. This is true for any multiple injection separation.

Figure 11:
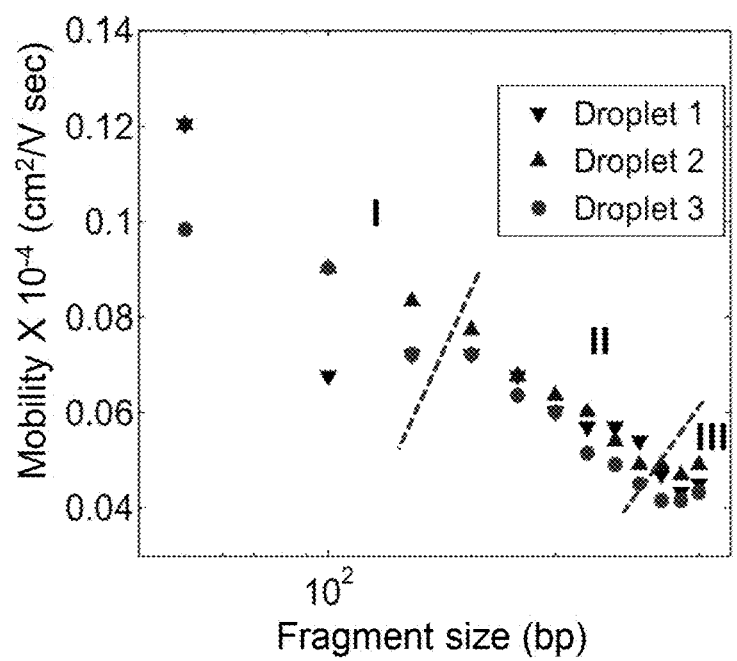
FIG. 11 shows a diagram of mobility vs. fragment size for three droplets, as determined from the electropherogram of FIG. 10.

As a control, FIG. 11 shows the capillary separation of the same ladder (unlabelled) in a capillary with total length of 54 cm and effective length of 42 cm.

The results from all of the different platforms showed a satisfactory consistency.

Example 4: Quantitative Electrophoresis

Figure 12:
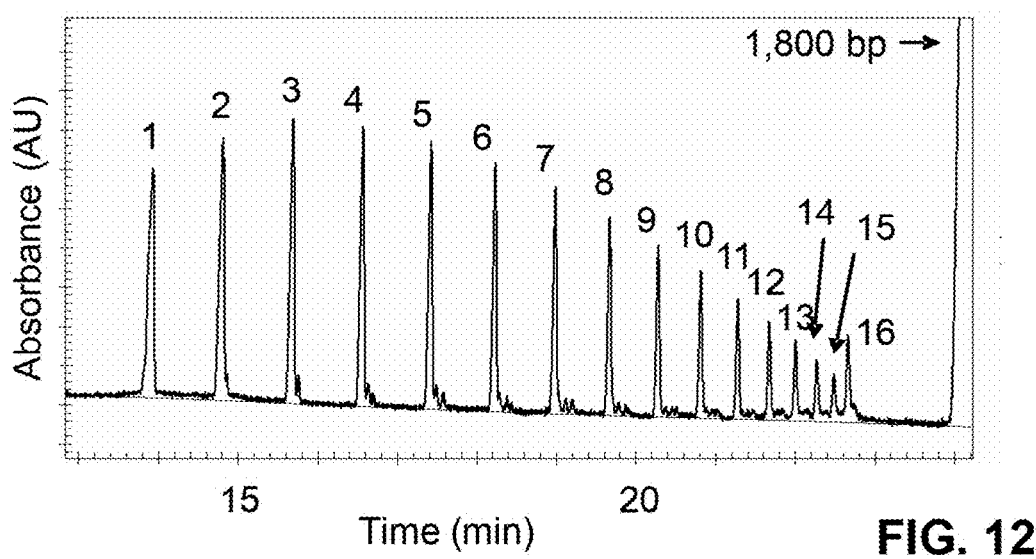
FIG. 12 shows an electropherogram for the molecular weight standard of FIG. 10 after separation in a longer capillary.
Figure 13:
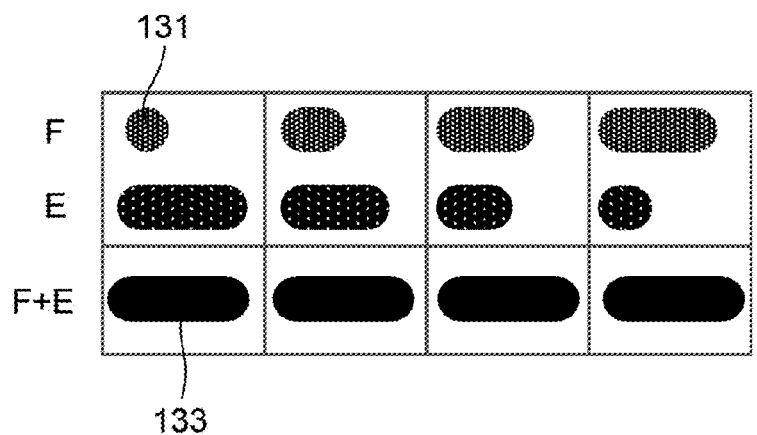
FIG. 13 shows an illustration of the composition of four droplets with varying concentrations of fluorescein and eosin dyes.
Figure 14:
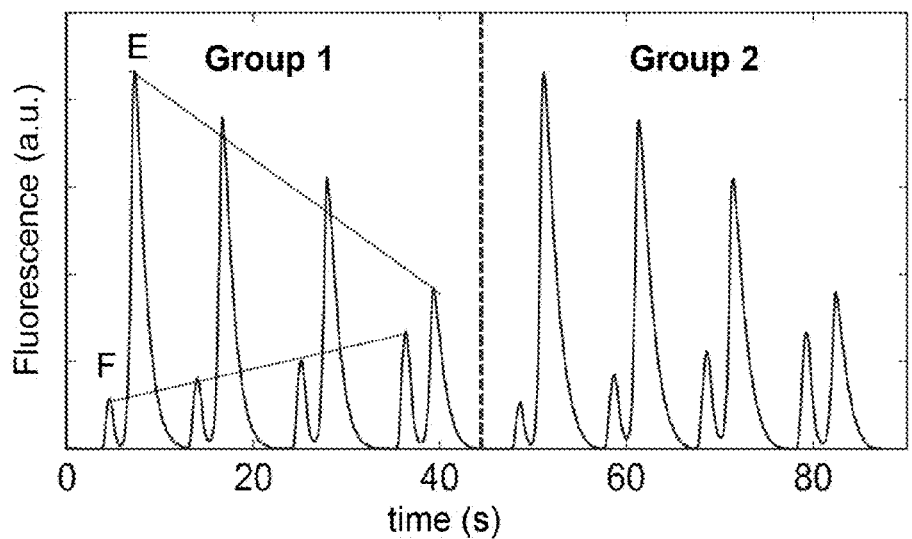
FIG. 14 shows electropherograms for two groups of four droplets each.
Figure 15:
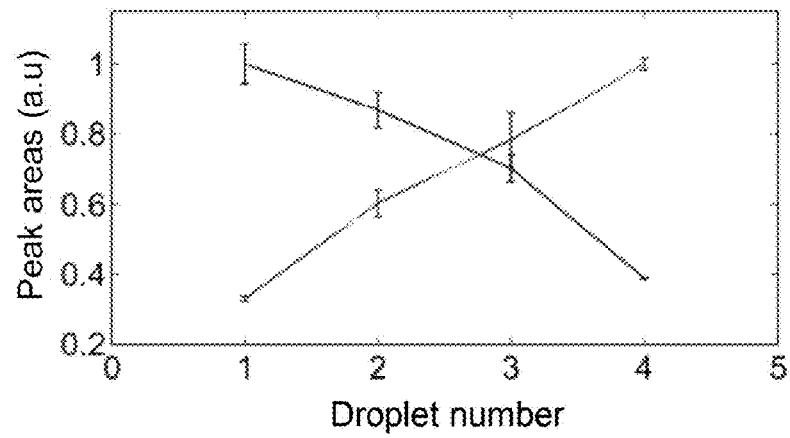
FIG. 15 shows a diagram of peak areas vs. droplet number.

Another advantage of the described droplet-CE interface is the ability to achieve high throughput injections of controlled volumes with no bias. Accordingly it is possible for such a CE separation to be used as a tool for quantitative analysis. This functionality was illustrated using a set of droplets with varying concentrations of fluorescein and eosin dyes (FIG. 12). Droplets were pre-generated with the Fluorescein concentration increasing from 6 to 9, 12, 15 μM and with the Eosin decreasing from 74 to 55, 37, 18.5 μM in 4 consecutive droplets with 4% volume variation. The fluorescein and eosin mix produced two peaks when separated using a 2.5% PEO sieving matrix. The separation results obtained for two groups of droplets is shown in FIG. 14. Peak areas for Fluorescein (F) and Eosin (E) were determined for each droplet. Linear fitting of the curves generated by each analyte showed $R2$ values above 0.9, indicating a good fit in both cases (FIG. 15). Consequently, the signal obtained from each droplet accurately reflected its concentration, permitting the generation of both calibration curves. Deviations from the fitted line were due to small variations in droplet size and manual error during sample preparation.

Overall, the present invention provides a droplet interfaced CE platform that is particularly suitable for biological separations. Such a platform is simple to operate and can process small sample volumes. The system can operate in high throughput, is free of inter contamination between samples, and is capable of quantitative analysis. Both CZE and CGE separations have been successfully achieved, showing the potential in a wide variety of applications such as small molecule separations, proteomics, genomics, metabolomics and the other chemical and biochemical assays.

Significantly, the platform detaches droplet generation and handling from the analytical separation, without decreasing the separation efficiency. Therefore, the vast majority of sample handling and preparation modules developed in droplet microfluidics can be integrated, for example, cell encapsulation and preparation in droplets, sample droplets collections from the other dimensional separations. The passive handling approach developed here can be readily integrated in a system with multiple parallel channels, with the potential for building up automated, multidimensional or multi-step separation and identification.

Experimental Details for Examples 3 and 4

(a) Materials and Sample Preparation

Fluorescein 5(6) Isothiocynate (FITC), Fluorescein and Eosin Y were obtained from Sigma (UK) along with ×1 Tris Borate EDTA (TBE, 89 Mm Tris, 89 Mm Borate and 2 mM ethylenediaminetetraacetic acid) and polyvinylpyrrolidone (PVP, average MW 360 kDa). Polyethylene oxide (PEO, >5 MDa) was obtained from Avocado Research Chemicals Ltd (Lancashire, UK). All buffers were made using 18 MΩ deionised water (Purite, Oxon, UK) and filtered using 5 μm pore membrane syringe filters (PALL Corporation, Hampshire, UK). Prior to use, the ×1 TBE was diluted 1 in 10 with water and used in this form for all experiments. Henceforward, this diluted version of ×1 TBE will be referred to as TBE. Bare fused silica capillaries were obtained from Polymicron Technologies. A 75 μm internal diameter and 375 μm outer diameter capillary was used for control experiment on a Peregrine HPCE instrument (deltaDOT, London, UK). The capillaries interfaced to the PDMS device had an internal diameter of 100 μm and an outer diameter of 375 μm.

FITC and Eosin Y were prepared at a stock concentration of 1.8 and 6 mg/ml respectively in water. Samples were further diluted 1000 times in TBE prior to droplet generation. The 50 bp dsDNA step ladder was obtained from Promega (Southampton, UK) while the SYBR Green I was obtained from Invitrogen (Paisley, UK). A ×500 stock of SYBR Green I was prepared in deionised water. The 50 bp ladder was diluted to 1/5 of the stock concentration in TBE and labelled with SYBR Green I at a final concentration of 1/100 of the stock concentration.

The Electrophoresis sieving medium was a 2.5% solution of polyethylene oxide (PEO) in TBE. The matrix was stirred for 24 hours and then filtered and degassed prior to use. Polyvinylpyrrolidone (PVP) solution was prepared at a 10% w/w concentration in water and was used to coat the capillary to neutralise EOF.

(b) Microfluidic Chip Fabrication and Operation

The microchip was fabricated using conventional soft lithographic techniques. First SU-8 was photo patterned on a Si wafer (IDB Technologies Ltd, North Somerset, UK) to form a master. After silanization, PDMS mixture (Dow Corning, Seneffe, Belgium), 10:1 weight ratio for the base and curing agent was poured on to the master and cured at 65° C. for 4 hours to yield a 4 mm thick PDMS channel substrate. The cured PDMS was subsequently peeled off and the buffer and waste reservoirs were punched out using a 4 mm biopsy punch (nu-careproducts, Bedfordshire, UK). 200 μm thick bare PDMS layer was used as the bottom substrate. The two layers were aligned and bonded together.

Capillaries were cut to obtain a flat surface at the end of insertion to the PDMS microdevice. The polyimide coating at this end was removed since it is not transparent and exhibits self-fluorescence. A 2 cm detection window was created by burning the polyimide coating from the capillary.

Prior to electrophoresis, capillaries were rinsed with methanol followed by deionized water. It was further cleaned with 0.1M HCl, then pre-coated with 10% PVP for 1 minute and then loaded with the sieving matrix (2.5% PEO). Such cleaning and conditioning prepossess were repeated after every 50 to 60 droplet injections.

Before use, chips were conditioned by rinsing the separation channel with 1 M NaOH or TBE. NaOH was used for the separations employing electroosmotic flow, while TBE was used for the CGE separations without EOF. This treatment was followed by loading the separation channel with the electrophoresis buffer. Prior to sample analysis, a conductivity check was performed by applying increasing voltages across the separation channel. The electric field was applied according to the direction of separation using a high voltage power supply (HVS448 3000V, Labsmith, Livermore, Calif., USA).

(c) Detection

Fluorescence images were collected using a fluorescence microscope (Eclipse 400, Nikon Ltd. Surrey, UK) with a CCD camera (C4742-96, Hamamatsu Photonic Systems, Bridgewater, N.J.). Briefly, light from a 100 W super high pressure mercury lamp was passed through a FITC filter cube before being focused on the detection region of the chip or capillary using ×10 objective lens. Fluorescent emission was collected with the same objective and detected with the camera. ImageJ software was used to analyze the videos recorded. Electropherograms were produced with Matlab (Mathworks).

The invention claimed is:

1. An oil removal device for removing oil from a stream of oil-separated sample droplets, the oil removal device comprising a sample delivery channel for conducting the stream of sample droplets separated by an oil phase along a first flow direction,
wherein the oil removal device comprises a porous, hydrophobic and oleophilic absorber element, the absorber element being in contact with the sample delivery channel so as to absorb the oil phase from the stream of oil-separated sample droplets, wherein a total pore volume or an oil-absorbing capacity of the absorber element exceeds a volume corresponding to the third power of the square root of a cross-sectional area of the sample delivery channel.

2. The oil removal device of claim 1, wherein the absorber element defines an irregular, three-dimensional network of pores.

3. The oil removal device of claim 1, wherein the absorber element is arranged at an outlet of the sample delivery channel, in a substantially tangential configuration relative to the first flow direction in the sample delivery channel.

4. The oil removal device of claim 3, wherein the absorber element at least partially surrounds the outlet of the sample delivery channel.

5. The oil removal device of claim 1, wherein the absorber element has a thickness that exceeds the diameter of the sample delivery channel at its outlet.

6. The oil removal device of claim 1, further comprising an aqueous flow channel for conducting a stream of aqueous liquid, the aqueous flow channel having a droplet inlet arranged to receive sample droplets from the outlet of the sample delivery channel.

7. The oil removal device of claim 6, wherein the aqueous flow channel has a carrier liquid inlet arranged upstream of the droplet inlet for receiving a continuous stream of aqueous carrier liquid, so as to conduct the carrier liquid through the aqueous flow channel along a second flow direction and to inject the sample droplets received at the droplet inlet into the stream of aqueous carrier liquid.

8. The oil removal device of claim 7, wherein, at the droplet inlet, the second flow direction extends substantially transverse to the first flow direction.

9. The oil removal device of claim 8, wherein the aqueous flow channel and the absorber element are each arranged in a laterally offset configuration relative to the sample delivery channel, the aqueous flow channel and the absorber element being arranged on mutually opposite sides of the sample delivery channel.

10. The oil removal device of claim 1, wherein the absorber element is a passive element to which no pressure difference is actively applied.

11. A method of removing oil from a stream of oil-separated aqueous sample droplets, the method comprising:
conducting the stream of sample droplets separated by an oil phase through a sample delivery channel to an outlet thereof; and
absorbing the oil phase from the stream of oil-separated sample droplets by a porous, hydrophobic and oleophilic absorber element arranged at the outlet of the sample delivery channel, wherein a total pore volume or an oil-absorbing capacity of the absorber element exceeds a volume corresponding to the third power of the square root of a cross-sectional area of the sample delivery channel.

12. The method of claim 11, further comprising:
feeding sample droplets from the outlet of the sample delivery channel to a droplet inlet of an aqueous flow channel.

13. The method of claim 12, further comprising:
conducting an aqueous carrier liquid through the aqueous flow channel; and
injecting the sample droplets received at the droplet inlet into the stream of aqueous carrier liquid.

14. The method of claim 13, wherein each sample droplet has such a length that, when a leading end of the sample droplet is positioned in the aqueous flow channel, a trailing end of the sample droplet still completely blocks the outlet of the sample delivery channel.

15. The oil removal device of claim 1, wherein the total pore volume or the oil-absorbing capacity of the absorber element exceeds ten times the volume corresponding to the third power of the square root of the cross-sectional area of the sample delivery channel.

16. The oil removal device of claim 1, wherein the total pore volume or the oil-absorbing capacity of the absorber element exceeds hundred times the volume corresponding to the third power of the square root of the cross-sectional area of the sample delivery channel.

17. The method of claim 11, wherein the total pore volume or the oil-absorbing capacity of the absorber element exceeds ten times the volume corresponding to the third power of the square root of the cross-sectional area of the sample delivery channel.

18. The method of claim 11, wherein the total pore volume or the oil-absorbing capacity of the absorber element exceeds hundred times the volume corresponding to the third power of the square root of the cross-sectional area of the sample delivery channel.

* * * * *